United States Patent [19]

Tsai

[11] Patent Number: 5,736,150
[45] Date of Patent: Apr. 7, 1998

[54] FAR-INFRARED RADIATING CREAM FOR EXTERNAL APPLICATION

[75] Inventor: Chung Yueh Tsai, Taipei, Taiwan

[73] Assignee: Fu Hsiang Textile Co., Ltd., Taipei, Taiwan

[21] Appl. No.: 769,007

[22] Filed: Dec. 17, 1996

[51] Int. Cl.⁶ ........................................ A61K 7/48
[52] U.S. Cl. ........................ 424/401; 514/617; 514/844
[58] Field of Search ........................... 424/401; 514/617, 514/844

[56] References Cited

U.S. PATENT DOCUMENTS 5,356,803  10/1994  Carpenter et al. .................. 435/200
5,395,541   3/1995  Carpenter et al. .................. 252/174.12
5,462,688  10/1995  Lippman et al. .................... 252/189.1

*Primary Examiner*—Jyothsan Venkat
*Attorney, Agent, or Firm*—Bacon & Thomas

[57] ABSTRACT

A far-infrared radiating cream for curing muscle ache and stiffness, composed of 4 wt % of a far-infrared radiating compound which is composed of 70 wt %–90 wt % of powdered perlite, 7 wt %–20 wt % of $Ta_2O_5$, 3 wt %–10 wt % $Nb_2O_5$, and 96 wt % of a cream which is composed of propylene, cetanol, squalane, paraffin oil, stearyl alcohol, glycine, propyl paraben, dL-α-tocopherol. The cream is capable of radiating far-infrared in the wavelength range of 3–16 μm when stimulated by body heat.

3 Claims, No Drawings

FAR-INFRARED RADIATING CREAM FOR EXTERNAL APPLICATION

BACKGROUND OF THE INVENTION

The present invention relates to creams for application to facial skin, and more particularly, to a far-infrared radiating cream for curing muscle ache and stiffness.

Various creams have been commercialized for applying to the skin of the face to vitalize the activity of cells, expand capillaries and promote metabolism. However, the effect of these creams does not last for long. Furthermore, regular creams for this purpose do not fit all people. Certain people may be allergic to a particular substance contained in creams. Therefore, improper use of creams may cause the skin of the face to be damaged.

SUMMARY OF THE INVENTION

It is the primary object of the present invention to provide a far-infrared radiating cream that produces heat to vitalize the activity of cells, expand capillaries and promote metabolism, a short length of time after its application to the user's face. It is another object of the present invention to provide a far-infrared radiating cream that provides curing effect to muscles ache and stiffens. It is still another object of the present invention to provide a far-infrared radiating cream that provides no side effect.

The far-infrared radiating cream for curing muscle ache and stiffness, is composed of 4 wt % of a far-infrared radiating compound which is composed of 70 wt %–90 wt % of powdered perlite, 7 wt %–20 wt % of $Ta_2O_5$, 3 wt %–10 wt % $Nb_2O_5$, and 96 wt % of a cream which is composed of propylene glycol, cetanol, squalane, paraffin oil, stearyl alcohol, glycine, propyl paraben, dL-α-tocopherol. The powdered perlite is composed of 73.41% of $SiO_2$, 12.34% of $Al_2O_3$, 1.33% $Fe_2O_3$, 2.95% $Na_2O$, 5.33% $K_2O$, and 3.70% of crystallized water. The cream is capable of radiating far-infrared in the wavelength range of 3–16 μm when stimulated by body heat.

DETAILED DESCRIPTION OF THE PREFERRED EMBODIMENT

Perlite is a kind of volcanic rock composed of 73.41% of $SiO_2$, 12.34% of $Al_2O_3$, 1.33% $Fe_2O_3$, 2.95% $Na_2O$, 5.33% $K_2O$, and 3.70% of crystallized water. It is commonly used as construction material, sound-absorbing plate, filtering agent, and fill. The perlite used by the present invention is powdered and sintered at 1100° C.–1300° C., for 3–8 hours. It has a purity of more than 99.9% and a granularity of 7–8 μm. Heated by low temperature such as that from the body's heat, the powder emits far-infrared radiation in the wavelength range of 3–16 μm. The amount of radiation can be significantly increased when the powdered perlite is mixed with powdered tantalum oxideμm ($Ta_2O_5$) and neodymium oxide ($Nb_2O_5$) in specific portions. These additives have a purity of more than 99.999% and a granularity of 17–20 μm.

The far-infrared radiating cream of the present invention is composed of 4 wt % of a far-infrared radiating compound that is composed of 70 wt %–90 wt % of powdered perlite, 7 wt %–20 wt % of $Ta_2O_5$, 3 wt %–10 wt % $Nb_2O_5$, and 96 wt % of a cream that is composed of propylene glycol, cetanol, squalane, paraffin oil, stearyl alcohol, glycine, propyl paraben, dL-α-tocopherol. This far-infrared radiating cream can emit far-infrared radiation in the wavelength range of 3–16 μm when it comes in contact with body heat. The radiation in this wavelength range provides strong heat-resonance effect to the skin, thereby generating heat that vitalizes the activity of cells, expands the capillaries, and promotes metabolism. The cream can be obtained, for example, from one of the following formulas (the percentage is measured by weight).

| Item | percentage |
| --- | --- |
| Example I: | |
| Water | 65.2% |
| Cetyl alcohol | 2.00% |
| Glycine monostearate | 3.50% |
| Estol-3575 | 7.00% |
| Paraffin oil | 8.00% |
| Stearic acid | 2.00% |
| Fragrance | 0.10% |
| Triethanol amine | 0.90% |
| Methyl paraben | 0.20% |
| Propyl paraben | 0.10% |
| Propylene glycol | 5.00% |
| $TiO_2$ | 2.00% |
| $SiO_2$ | 4.00% |
| Example II: | |
| Water | 60.285% |
| C12–20 Acid peg-8 ester | 15.00% |
| Mimeral oil | 5.500% |
| Petrolatium | 5.00% |
| Acetyated lanolin | 2.00% |
| Horsetail extract | 1.00% |
| Triethanol amine | 1.55% |
| Carbomer | 1.50% |
| Potassium cetyl phosphate | 0.45% |
| Phenoxyethanol | 1.42% |
| Fragrance | 0.25% |
| Imidazolidinyl urea | 1.22% |
| TRCLOSAN | 0.825 |
| $SiO_2$ | 4.00% |
| Example III: | |
| Water | 75.5355% |
| Mineral oil | 4.675% |
| C12–20 Acid peg-8 ester | 5.50% |
| Propylene glycol | 2.75% |
| Petrolatium | 3.00% |
| Horsetail extract | 1.50% |
| Acetyated | 1.00% |
| Triethanol amine | 0.45% |
| Imidazolidinyl urea | 0.22% |
| Fragrance | 0.20% |
| TRCLOSAN | 0.75 |
| Carbomer | 0.45% |
| Potassium cetyl phosphate | 0.45% |
| Squalane | 0.45% |
| Butylparaben | 0.42% |
| $SiO_2$ | 4.00% |

The cream prepared from either one of the aforesaid three formulas is then mixed with the aforesaid far-infrared radiating compound at the ratio of 96 wt % of the cream with 4 wt % of the far-infrared radiating compound.

When in use, the far-infrared radiating cream is directly applied to the skin of the face. A certain length of time after application, heat is generated to vitalize the activity of cells, expand capillaries and promote metabolism.

I claim:

1. A far-infrared radiating cream comprising 4 wt % of a far-infrared radiating compound and 96 wt % of a cream, said far-infrared radiating compound comprising 70 wt %–90 wt % of powdered perlite wherein said perlite is comprised of 73.41% of $SiO_2$, 12.34% of $Al_2O_3$, 1.33% $Fe_2O_3$, 2.95% of $Na_2O$, 5.33% of $K_2O$, and 3.70% of crystallized water and wherein said perlite has a purity of more than 99.9% and a granularity in the range of 7–8 μm, 7 wt %–20 wt % of $Ta_2O_5$, and 3 wt %–10 wt % $Nb_2O_5$, said cream being comprised of propylene glycol, cetanol, squalane, paraffin oil, stearyl alcohol, glycine, propyl paraben, dL-α-tocopherol.

2. The far-infrared radiating cream of claim 1 wherein said powdered perlite has been sintered at a temperature in the range of 1100° C.–1300° C., for a period in the range of 3–8 hours.

3. The far-infrared radiating cream of claim 1 wherein said $Ta_2O_5$ and said $Nb_2O_5$ have a purity of 99.9% and a granularity in the range of 17–20 μm.

* * * * *